(12) United States Patent
Gladue et al.

(10) Patent No.: US 11,796,548 B2
(45) Date of Patent: Oct. 24, 2023

(54) CONTINUOUS STABLE CELL LINE FOR IDENTIFICATION OF INFECTIOUS AFRICAN SWINE FEVER VIRUS IN CLINICAL SAMPLES

(71) Applicant: The United States of America, as represented by the Secretary of Agriculture, Washington, DC (US)

(72) Inventors: Douglas P. Gladue, Guilford, CT (US); Ayushi Rai, Old Saybrook, CT (US); Manuel V. Borca, Westbrook, CT (US)

(73) Assignee: The United States of America, as represented by The Secretary of Agriculture, Washington, DC (US)

( * ) Notice: Subject to any disclaimer, the term of this patent is extended or adjusted under 35 U.S.C. 154(b) by 253 days.

(21) Appl. No.: 17/236,284

(22) Filed: Apr. 21, 2021

(65) Prior Publication Data

US 2021/0333293 A1   Oct. 28, 2021

Related U.S. Application Data

(60) Provisional application No. 63/013,660, filed on Apr. 22, 2020.

(51) Int. Cl.
| | | |
|---|---|---|
| *C12N 7/00* | (2006.01) | |
| *C12N 7/01* | (2006.01) | |
| *G01N 33/80* | (2006.01) | |
| *G01N 33/569* | (2006.01) | |
| *G01N 33/53* | (2006.01) | |

(52) U.S. Cl.
CPC .............. *G01N 33/80* (2013.01); *C12N 7/00* (2013.01); *C12N 2710/12031* (2013.01); *G01N 2333/01* (2013.01); *G01N 2800/26* (2013.01)

(58) Field of Classification Search
CPC ............ C12N 2710/12031; C12N 7/00; C12N 2710/12051; G01N 2800/26; G01N 33/56983
See application file for complete search history.

(56) References Cited

U.S. PATENT DOCUMENTS

| | | |
|---|---|---|
| 2005/0271684 A1 | 12/2005 | Calvert et al. |
| 2010/0158947 A1 | 6/2010 | Delputte et al. |
| 2014/0004504 A1* | 1/2014 | Wangh .................. C12Q 1/701 435/5 |

OTHER PUBLICATIONS

International Search Report from PCT/US2021/028570, dated Aug. 9, 2021.
De Leon, P. et al., 'Laboratory methods to study African swine fever virus', Virus Research, 2013, vol. I 73, pp. 168-179.
Sanchez-Torres, C. et al., 'Expression of porcine CD 163 on monocytes/macrophages correlates with permissiveness to African swine fever inl'cction', Arch. Virol., 2003, vol. 148, pp. 2307-2323.
Londrigan, S. L. et al . . . 'Growth of rotaviruses in continuous human and monkey cell lines that vary in their expression of integrins', Journal of General Virology, 2000, vol. 81, pp. 2203-2213.
Rai, A. et al., 'Identification of a Continuously Stable and Commercially Available Cell Line for the Identification of Infectious African Swine Fever Virus in Clinical Samples', Viruses. Jul. 28, 2020, vol. 2, Article 820, pp. 1-7.

* cited by examiner

*Primary Examiner* — Barry A Chestnut
(74) *Attorney, Agent, or Firm* — John D. Fado; Mark D. McNemar

(57) ABSTRACT

Methods are provided herein utilizing a stable cell line capable of efficient infection by African swine fever virus (ASFV) and also provides for the detection of the presence of virus in samples applied to the cells. Detection of the virus by means such as red blood cell rosetting is a surprising result given that the cell line is derived from African green monkeys. This cell line provides a marked improvement over the currently available testing strategies.

11 Claims, 3 Drawing Sheets
(2 of 3 Drawing Sheet(s) Filed in Color)

FIG. 2

CONTINUOUS STABLE CELL LINE FOR IDENTIFICATION OF INFECTIOUS AFRICAN SWINE FEVER VIRUS IN CLINICAL SAMPLES

CROSS-REFERENCE TO RELATED APPLICATIONS

The present application claims priority to U.S. Provisional Patent Application Ser. No. 63/013,660 filed Apr. 22, 2020, the content of which is expressly incorporated herein by reference.

BACKGROUND OF THE INVENTION

Field of Invention

The instant disclosure provides a stable cell line capable of supporting the growth of African swine fever virus (ASFV) and also provides for the detection of the presence of virus in samples applied to the cells. Detection of the virus by means such as red blood cell rosetting is a surprising result given that the cell line is derived from African green monkeys. This cell line provides a marked improvement over the currently available testing strategies.

Background

ASFV is the only member of the virus family Asfarviridae and the etiological agent that causes African swine fever (ASF). This large double stranded DNA virus has more than 150 ORFs that are encoded in the 180-190 kilobase genome. ASF disease can range from sub-clinical to lethal depending both on the specific host that is infected and the specific strain of virus (Tulman et al, "African Swine Fever Virus", p. 43-87, in "Lesser Known Large dsDNA Viruses," Springer-Verlag Berlin Heidelberg (2009)). Several sub-Saharan African countries and Sardinia (Italy) have endemic ASF. Recent outbreaks of ASFV started with only a single introduction of ASFV in the Caucasus region in 2007. This outbreak affected Georgia, Armenia, Azerbaijan and Russia and more recently has spread as far west as Poland causing the fear that this disease could disseminate into other neighboring European countries (Chapman, et al, Emerg. Infect. Dis., (2011) 17:599-605). Importantly, the disease spread east, reaching China and south east Asian countries. The concern is due to the current outbreak strain which can be highly contagious and in domestic pigs it often causes lethality. Due to the potential and widespread loss of domestic pigs, the swine industry could suffer from substantial economic consequences should an outbreak occur (Costard et al, Philos. Trans. R. Soc. London B Biol. Sci., (2009) 364:2683-96).

There are no vaccines currently available to prevent ASF, and control of outbreaks has relied on quarantine and culling of infected or exposed animals. Diagnosis of ASFV in clinical samples, mainly blood, is done though real time PCR, however real time PCR cannot detect the difference between live infectious virus, or virus that is no longer infectious. A confirmatory test is needed, that involves identifying infectious virus in cell culture and currently can only be done in primary swine macrophages. Detection of infectious virus is of paramount importance in the epidemiological management of a disease outbreak in an ASF-free area. Primary swine macrophages are very time and labor consuming to produce, and are often not readily available, as they need to be newly collected from swine blood or isolated from lungs.

Previous studies have shown that ASFV can be adapted to cell lines, however these adaptations take many passages and are not suitable for virus isolation from field samples. Therefore, we sought to identify a cell line that was capable of virus isolation from field samples at a sensitivity comparable to that of primary swine macrophages. As a result of our efforts we unexpectedly discovered that certain African green monkey cells named Ma-104 (ATCC #CRL2378) can be utilized instead of primary swine macrophages for ASFV virus isolation and detection.

SUMMARY OF THE INVENTION

In one part, the present application provides a method of detecting African Swine Fever Virus (ASFV) in a sample, comprising the steps of: 1) contacting the sample with a culture of Ma-104 cells under conditions that allow for infection of the cells by ASFV; 2) incubating the Ma-104 cell and sample mixture under conditions that allow for ASFV detection; and 3) analyzing the mixture from step b for the presence or absence of replicating ASFV. In some embodiments, the ASFV is a strain of ASFV that is not attenuated for growth in Ma-104 cells. In preferred embodiments, the ASFV utilized for this method is a strain of ASFV that has not been passaged in cell culture prior to contacting with Ma-104 cells. In a specific embodiment, the ASFV is of the Georgia/2007 strain. Samples analyzed can comprise a sample from a swine, such as a pig or boar. In some embodiments, the analyzing step of the method is performed by adding red blood cells to the sample/Ma-104 mixture, and examining the Ma-104 cells for the presence or absence of hemadsorbed red blood cells on the Ma-104 cells. In specific embodiments of this version of the method, the presence or absence of hemadsorbed red blood cells is determined within 24 hours after the red blood cells are added to the Ma-104 cell and sample mixture.

An additional embodiment provided herein is a composition composed of Ma-104 cells, African Swine Fever Virus (ASFV), and red blood cells. In some specific embodiments, the ASFV of the composition is the Georgia/2007 strain.

INCORPORATION BY REFERENCE

All publications, patents and patent applications mentioned in this specification are herein incorporated by reference to the same extent as if each individual publication, patent or patent application was specifically and individually indicated to be incorporated by reference.

BRIEF DESCRIPTION OF THE DRAWINGS

The patent application file contains at least one drawing executed in color. Copies of this patent or patent application publication with color drawing(s) will be provided by the Office upon request and payment of the necessary fee.

The novel features of the invention are set forth with particularity in the claims. Features and advantages of the present invention are referred to in the following detailed description, and the accompanying drawings of which:

Figure 2:
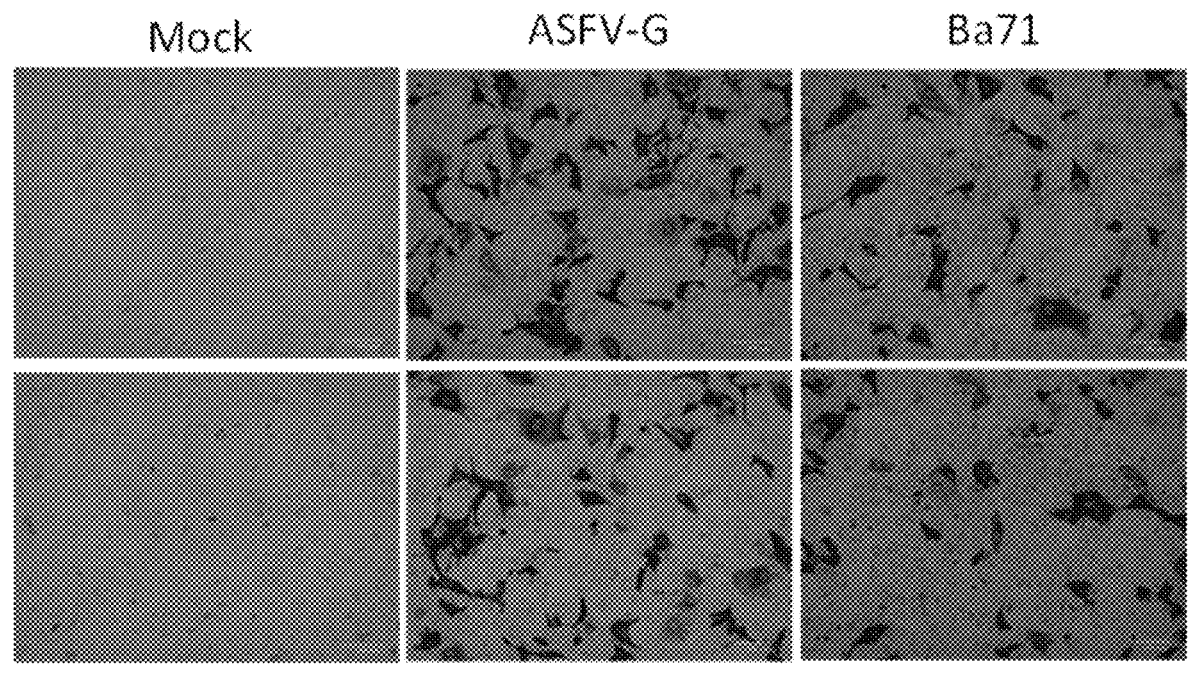

FIG. 2 provides micrographs depicting immunohistochemical staining of Ma-104 and primary swine macrophages with antibodies specific for the ASFV p 30 protein.

DETAILED DESCRIPTION OF THE INVENTION

Figure 1:
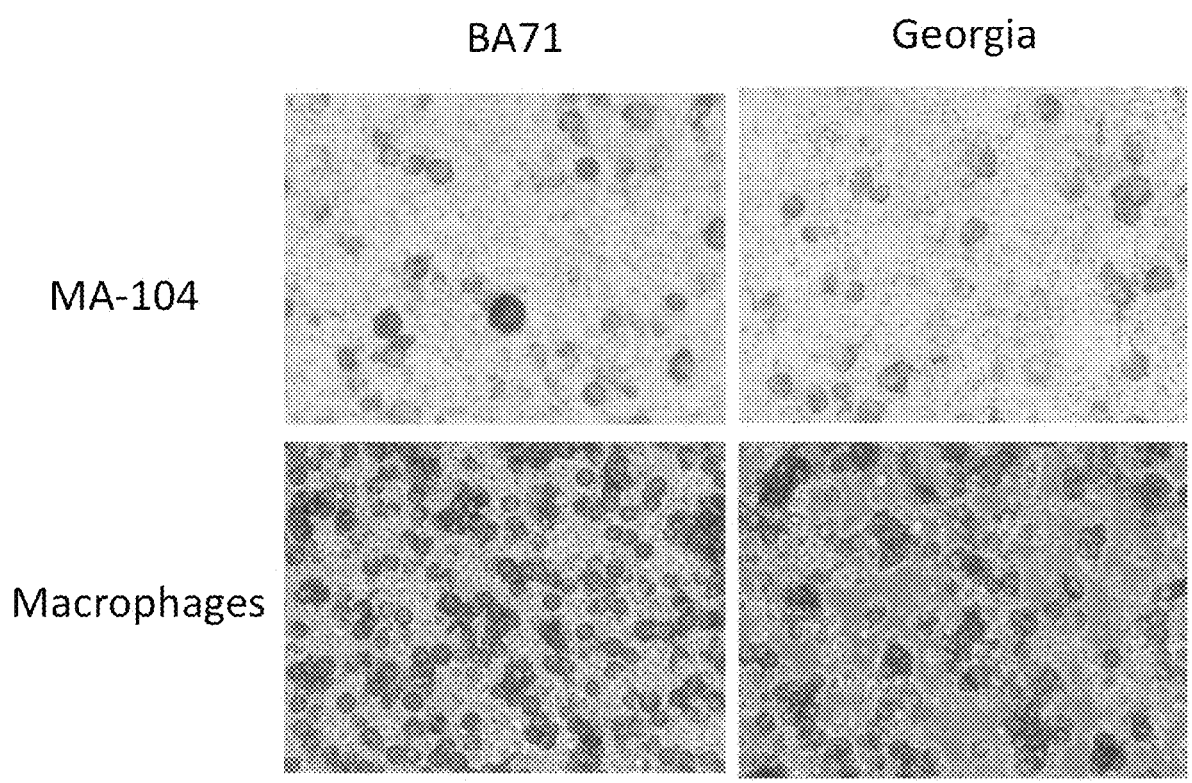
FIG. 1 provides micrographs depicting the results of hemadsorption assays performed on primary swine macrophages and Ma-104 cells.
Figure 3:
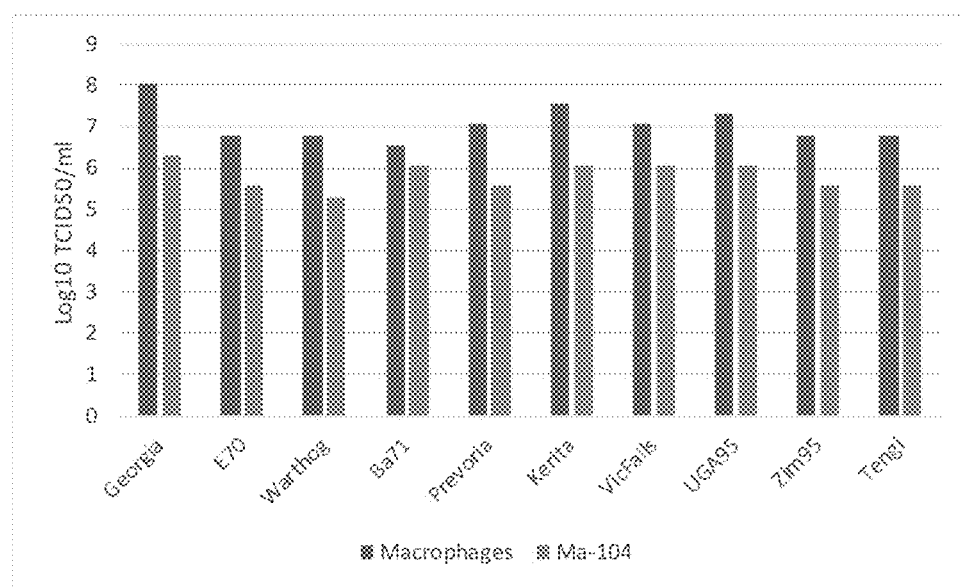
FIG. 3 provides a graph representing the relative detection of various ASFV field isolates utilizing Ma-104 versus primary swine macrophages.

African swine fever virus (ASFV) is causing outbreaks both in domestic pigs and wild boar in Europe and Asia. In 2018 the largest pig producing country, China, reported the first outbreak of ASF. Since then, the disease has quickly spread to all provinces in China and to other countries in southeast Asia. Outbreaks of the disease occur in Europe as far west as Poland, and one isolated outbreak has been reported in Belgium. The current outbreak strain is highly contagious and can cause in domestic pigs a high degree of lethality, leading to widespread and costly losses to the industry. Currently diagnosis of ASFV positive samples relies on only PCR, which cannot distinguish between infectious and non-infectious virus in positive samples. Currently there is no virologic test, as the only cellular substrate for virus isolation of field samples is primary swine macrophages. Here we report the identification of a commercially available cell line Ma-104 as a suitable substrate for ASFV isolation and detection.

Preferred embodiments of the present invention are shown and described herein. It will be obvious to those skilled in the art that such embodiments are provided by way of example only. Numerous variations, changes, and substitutions will occur to those skilled in the art without departing from the invention. Various alternatives to the embodiments of the invention described herein may be employed in practicing the invention. It is intended that the included claims define the scope of the invention and that methods and structures within the scope of these claims and their equivalents are covered thereby.

Technical and scientific terms used herein have the meanings commonly understood by one of ordinary skill in the art to which the instant invention pertains, unless otherwise defined. Reference is made herein to various materials and methodologies known to those of skill in the art.

Any suitable materials and/or methods known to those of skill can be utilized in carrying out the instant invention. Materials and/or methods for practicing the instant invention are described. Materials, reagents and the like to which reference is made in the following description and examples are obtainable from commercial sources, unless otherwise noted. This invention teaches methods and describes tools for detecting ASFV in samples using a stable cell line.

As used in the specification and claims, use of the singular "a", "an", and "the" include plural references unless the context clearly dictates otherwise.

The terms isolated, purified, or biologically pure as used herein, refer to material that is substantially or essentially free from components that normally accompany the referenced material in its native state.

The term "about" is defined as plus or minus ten percent of a recited value. For example, about 1.0 g means 0.9 g to 1.1 g and all values within that range, whether specifically stated or not.

The term "Ma-104", refers to the commercially available, stable cell line derived from African green monkey cells and available from the American Type Culture Collection under the designation "ATCC #CRL2378". The term can also include genetically modified cells and cell lines derived from Ma-104.

ASFV Field Isolates

African swine fever virus (ASFV) is the causative agent of the pandemic disease currently affecting pigs all over Eurasia causing significant economic consequences to the swine industry. There is limited cross protection between different strains of the virus and has led to genotyping of the virus into over 20 genotypes by sequencing of specific genes structural protein p54 or p72 and CVR (central variable region). Field strains, or field isolates, are derived from infected domestic or wild suids, that are showing symptoms of the disease, or samples were collected from routine surveillance. Currently in Europe and Asia a highly virulent field isolate termed Georgia/2007 is circulating, this isolate is genotypically the same as all lethal isolates currently in that region. Historically other genotypes have been found in different parts of the world, namely in Africa where it is unknown how many are currently circulating in the wild population. It is not uncommon for an ASFV isolate to be attenuated in one suid species and virulent in domestic swine. Attenuated field isolates have also been recovered from surviving pigs also belonging to genotype II, such as one recovered in Latvia (PMID: 30667598). Some other examples of other ASFV field isolates include BA71, E75 (genotype I), Tengani (genotype 5), Zim (genotype 18), Uganda/95 (genotype 9).

Historically infectious ASFV could only be detected using primary swine macrophages of pulmonary or bone marrow origin. Attempts to grow ASFV in established cell lines have required several passages of adaptation, where often the field isolate is lost. However, when successful, these cell-culture-adapted strains have undergone important genomic changes and usually became attenuated in swine (PMID: 25505073). Additionally, non-adapted ASFV does not grow significantly (low virus yield) in cell lines, does not efficiently infect the cell lines, and cannot be easily detected in cell lines. Thus, cell lines have not been useful for the identification of ASFV field isolates (i.e., ASFV that is not passaged multiple times to become cell-culture adapted).

Virus Detection

Provided herein are methods for detecting viruses in samples from subjects (such as swine, including pigs, boars, warthogs, etc.). Samples from such subjects can be taken from any relevant body site (e.g., nasal, oropharyngeal, anal) or tissue (e.g., blood, sputum, feces). In practicing the methodologies herein, the skilled artisan can select an appropriate sample source. In some instances, more than one sample from a single subject can be tested. Sample collection and sample storage methodologies are well known in the art, and any such methodologies can be utilized in practicing the present disclosure. For the present disclosure, such detection methods include the step of exposing Ma-104 cells (or cells derived from Ma-104) to the collected sample to determine the presence or absence of ASFV.

A preferred approach to practicing the present disclosure is to use a hemoadsorption (hemadsorption) assay (HA) to detect the presence of ASFV in a sample that has been exposed to Ma-104 cells. Without being bound by mechanism, HA is contingent on the attachment of red blood cells to the surface of cells in monolayers or suspension that are infected with enveloped, hemagglutinin-producing viruses, such as ASFV. Generally, a red blood cell suspension is incubated with an infected cell culture. If the virus (e.g., ASFV) reproduces sufficiently in that cell culture, hemadsorption is observed as a result of ASFV viral protein Ep402R (also called 8DR and CD2-like) being expressed. This protein causes attachment of red blood cells to infected cells, when this protein is deleted, hemadsorption no longer occurs in infected cells (PMID: 31949276, 9525608). It is at these modified areas of the cell surface that red blood cells will specifically bind. Thus, the presence of red blood cells on the surface of the cultured cells indicates the presence of hemadsorption and the presence of viral growth. As hemadsorption is well established to only occur while the virus expresses its proteins as a prelude to viral maturation, a positive HA result indicates the presence of infectious ASFV in the cell.

Some level of random cellular uptake of ASFV is often observed in stable cell lines when in contact with high concentrations of virus. However, it is surprising that Ma-104 cells are able to detect low levels of infectious virus with a similar efficiency as compared to primary swine macrophages.

An additional approach to virus detection utilizes nucleic-acid-based methods, such as sequencing or polymerase chain reaction (PCR). In particular embodiments, real-time PCR can be utilized targeting any ASFV sequence relevant to the strain(s) of ASFV detected. Targeted sequences can be viral genomic sequences, or expressed sequences (e.g., mRNA, cDNA). Such sequences include, but are not limited to p30, p72, and p54. The techniques for performing such analyses are well known in the art, and the parameters for testing for one or more target sequences are readily determined by those skilled in the art.

Immunohistochemical analysis, or immunostaining, can also be utilized to determine the presence of ASFV in Ma-104 cells. Generally, antibodies that specifically bind to an ASFV protein are used to detect the presence of ASFV in the cells. The antibodies can be conjugated to labels that allow for detection, such as gold nanoparticles, enzymes that catalyze a colorimetric reaction, and fluorophores. The materials and methodologies for performing such analyses are well known in the art. ASFV proteins that can be targeted utilizing such approaches are limited as commercial antibodies only exist for a few structural proteins, including p30, p54 and p72.

Having generally described this invention, the same will be better understood by reference to certain specific examples, which are included herein to further illustrate the invention and are not intended to limit the scope of the invention as defined by the claims.

EXAMPLES

Example 1

Animal Studies, Cell Lines, Viruses and Immunoperoxidase Staining

Blood samples used in this study were collected as part of a previous study described in previous studies for ASFV-G (unpublished study 2018) and ASFV-Pretoria (Carlson et al, Viruses, (2016) 8:10. Samples were frozen since the time of the study at −70° C.

Primary swine macrophage cell cultures were prepared from defibrinated swine blood as previously described (Zsak, et al, J. Virol., (1996) 70:8865-71) and were then reseeded into Primaria, 6- or 96-well dishes at a density of $5 \times 10^6$ cells per ml for use in assays 24 hours later. Ma-104 cells were plated in 6- or 96 well plates at a density of $5 \times 10^6$ and used in assays immediately.

ASFV Georgia (ASFV-G) was a field isolate kindly provided by Dr. Nino Vepkhvadze, from the Laboratory of the Ministry of Agriculture (LMA) in Tbilisi, Republic of Georgia. E70 was provided by J. M Escribano (INIA Madrid Spain). The other ASFV isolates tested in this study are part of Plum Island Animal Disease Center Reference collection: Warthog Assession number: AY261366.1 collected before 2003 from an infected warthog (reference gara report), Ba71 Assession number KP055815 isolated in Spain (1971-1975) (PMID: 26589145), Pretoriuskop/96/4 (Pret4) Assession number #AY261363 collected in 1996 in South Africa Kruger National park (Kerita (KE), Victoria Falls (VI), Uganda95 (UG), Zimbabwe95 (ZM) and Tengani (TE) (PMID: 6296285).

Ma-104 cells were plated as described above, Primary swine macrophage cell cultures were prepared from defibrinated swine blood as previously described (Zsak, et al, J. Virol., (1996) 70:8865-71) and were then reseeded into Primaria, 96-well dishes at a density of $5 \times 10^6$ cells per ml for use in assays 24 hours later.

Titrations were performed side by side in primary swine macrophages and Ma-104 cells using viral stocks for isolates described above and after 5 days in culture, cells were read for titration by TCID50 using hemadsorption. Titers were calculated according to the method of Reed and Muench (Am. J. Hygiene, (1938) 27:493-7)

Immunoproxidase staining was performed by Ma-104 cells or Swine macrophages fixed with acetone and methanol (50:50) for 15 minutes. Viral infectivity was assessed using an immunoperoxidase assay with an ASFV monoclonal antibody for detecting ASFV p30 at a 1:200 dilution using a Vectastain ABC kit (Vector Laboratories, Burlingame, Calif.). Titers were calculated according to the method of Reed and Muench (supra).

Animal experiments to collect blood for swine macrophages were performed under biosafety level 3AG conditions in the animal facilities at Plum Island Animal Disease Center (PIADC). All experimental procedures were carried out in compliance with the Animal Welfare Act (AWA), the 2011 Guide for Care and Use of Laboratory Animals, the 2002 PHS Policy for the Humane Care and Use of Laboratory Animals, and U.S. Government Principles for Utilization and Care of Vertebrate Animals Used in Testing, Research and Training (IRAC 1985), as well as specific animal protocols reviewed and approved by the PIADC Institutional Animal Care and Use Committee of the US Departments of Agriculture and Homeland Security (protocol number 225.04-16-R, 09-07-16).

Example 2

Detection of ASFV Infected Ma-104 Cells by Hemoadsorption

Hemoadsorption (HA) or the ability of ASFV-infected cells to form rosettes in the presence of red blood cells is an easy visual test for ASFV isolation in cell culture. Swine macrophages or stable cell lines were plated at the density of $5 \times 10^6$ cells/ml in 6-well tissue culture dishes. Cells were infected, or mock infected, using an MOI of 1 of the current outbreak strain (Georgia/2007, a genotype II strain), or strain Ba71 (a genotype I strain). At one-hour post infection (hpi), 100 ul of 25% of red blood cells were added to each well. Twenty-four hpi the cells were observed for the presence of ASFV by the ability to form rosettes in a HA assay (FIG. 1). We observed that Ma-104 Cells could form rosettes comparably to that of swine macrophages.

Example 3

Immunohistochemical Staining of ASFV Infected Ma-104 Cells

HA relies on the presence of a functional CD2-like gene in ASFV. Some natural isolates have been shown to have mutations in CD2 where they are unable to form rosettes. To determine if Ma-104 cells could be used as a substrate for cell staining with monoclonal antibody specifically recognizing ASFV protein p30. Swine macrophage or stable cell lines were plated at the density of $1\times10^6$ cells/ml in 6-well tissue culture dishes. Cells were infected or mock infected using an MOI of 1 of current outbreak strain Georgia/2007 a genotype II stain or Ba71 a genotype I stain of ASFV. After 24 hours cells were fixed and stained as described in the material and methods. We saw very clear positive staining (FIG. 2) in both swine macrophages and Ma-104. Indicating that Ma-104 could be used as an alternative substrate for staining of ASFV, and identification of ASFV isolates that do not display HA due to disruption in CD2.

Example 4

Comparing Relative Sensitivity of Ma-104 Cells and Primary Swine Macrophages for Detecting Different ASFV Field Isolates The relative sensitivity of Ma-104 cells to detect infectious ASFV was evaluated in comparison to that of primary swine macrophages. Different ASFV virus field isolates from our archived ASFV virus collection were used and their infectivity was quantified by virus titration performed in parallel in both swine primary macrophage cells and Ma-104 cells. Swine macrophages were plated the day before at $1\times10^6$ cells per 96-well plate while Ma-104 cells were plated at a concentration of $1\times10^6$ cells per 96-well plate and used immediately after plating. Ten-fold serial dilutions of the viruses were prepared in macrophage media and each of the dilutions were seeded either in swine macrophages or Ma-104 cells. The cells were incubated at 37° C. at 5% $CO_2$ and, 24 hours later, 1 ul of 30% red blood cells were added to each well. After 7 days at 37° C., presence of infected cells was detected by HA (rosette formation) the titers were calculated using the Reed and Muench method and expressed as $\log_{10}$ $HAD_{50\%}$/ml. In all cases the difference in virus titrations in Ma-104 cells when compared to primary swine macrophages was approximately 1 $\log_{10}$ (with the average among all viruses tested being 1.275 logs) lower than in swine macrophages. All viruses tested were able to form rosettes at a similar level to the Georgia/2007 strain (FIG. 3)

Example 4

Comparison of Real-Time PCR (RT-PRC) Sensitivity

To further confirm the sensitivity of Ma-104 cells, virus dilutions used for titrations were compared to real time PCR using a validated in-house RT-PCR protocol as previously described. Real time PCR was found to be as equally sensitive as virus isolation on Ma-104 cells and was directly compared for the isolates in Example 3.

Example 5

Multiple Cell Lines Tested

We tested other cell lines with an infectious ASFV expressing a fluorescent reporter (PMID: 28436458) of different animal origins including Swine kidney cells (SK6), African Green monkey kidney cells (Vero, Cos 1), Wild boar cells (WSL), or immortalized swine macrophage cell lines (zMAC, 3D4/31 (ATCC CRL-2844), 3D4/2 (ATCC CRL-2845) in all of these cell lines only very few cells (<1%) were positive by fluorescence. This very low level of fluorescence appears to be from non-specific uptake of the virus, which allows a low level of viral protein translation allowing the expression of the fluorescent reporter. In the case of Ma-104 cells, however, a surprisingly and unexpectedly large percentage of cells become infected with fluorescence observed in a similar level of detection to results observed in primary swine macrophages, which was a surprising result as we did not observe this with any other cell line tested.

Example 6

Blood samples used in this study were collected as part of a previous study described in previous studies for ASFV-G (unpublished study 2018) and ASFV-Pretoria (Carlson et al. Viruses. 2016 Oct. 22; 8(10). Samples were frozen since the time of the study at −70° C.

Primary swine macrophage cell cultures were prepared from defibrinated swine blood as previously described (Zsak, et al, J. Virol., (1996) 70:8865-71) and were then reseeded into Primaria, 6- or 96-well dishes at a density of $5\times10^6$ cells per ml for use in assays 24 hours later. Ma-104 cells were plated in 6- or 96 well plates at a density of $5\times10^6$ and used in assays immediately.

Blood samples plated in both 6 well plates or 96 well plates and were observed for 24 hrs where they showed positivity for ASFV in clinical samples by hemeadsorption for samples that were previously shown positive by in macrophages (data not shown).

Example 7

Testing of sensitivity of clinical samples will be performed using blood from different genotypes that are available from previously performed animal studies, including isolates such as Georgia, Pretoria and Ba71. We will compare the sensitivity of these samples in Ma-104 to that of swine macrophages, we expect to see similar results in both Ma-104 and swine macrophages. As we were able to detect ASFV in both cell lines in clinical blood samples, and have observed similar titers using viral stocks produced in primary swine macrophages.

Example 8

Quantitation of Hemadsorption Levels

In order to quantitate the level of hemadsorption we performed titrations using the standard reed and Munich method typically used to quantitate ASFV, and determined similar levels of ASFV in MA104 cells as in swine macrophages.

It is also unexpected that MA-104 cells are able to efficiently show clear hemadsorption at levels that are similar to that of primary swine macrophages. Presence of infectious ASFV is confirmed using hemadsorption in primary swine macrophages. In Ma104 cells the level of hemadsorption is similar to swine macrophages, which would allow for Ma104 cells to be used as an alternative cell substrate for detecting live ASFV in Ma104 cells.

In Ma-104 cells infected with recombinant ASFV expressing a fluorescent reporter the same infectious rate was observed with both fluorescence and HA. Although this result does not apply to field strains that will not contain a fluorescence marker, it is important to understand that in Ma-104 all infected cells are capable of showing HA, which was not the case in other cell lines tested, as only a low level of background fluorescence was observed.

To further evaluate the difference between Ma-104 cells and cell lines such as vero or cos 1, which after virus adaption, which takes several blind passages, and is often not successful, titrations using a field isolate of ASFV-G will be compared to primary swine macrophages to show quantitively the lack of the ability to detect ASFV field strains.

While the invention has been described with reference to details of the illustrated embodiments, these details are not intended to limit the scope of the invention as defined in the appended claims. The embodiment of the invention in which exclusive property or privilege is claimed is defined as follows:

What is claimed is:

1. A method of detecting African Swine Fever Virus (ASFV) in a sample, comprising the steps of:
   a. contacting the sample with a culture of Ma-104 cells under conditions that allow for infection of the cells by ASFV;
   b. incubating the Ma-104 cell and sample mixture under conditions that allow for ASFV detection; and
   c. analyzing the mixture from step b for the presence or absence of replicating ASFV.

2. The method of claim 1, wherein the ASFV comprises a strain of ASFV that is not attenuated for growth in Ma-104 cells.

3. The method of claim 1, wherein the ASFV comprises a strain of ASFV that has not been passaged in cell culture prior to contacting with Ma-104 cells.

4. The method of claim 1, wherein the ASFV comprises the Georgia/2007 strain.

5. The method of claim 1, wherein the sample comprises a sample from a swine.

6. The method of claim 1, wherein the analyzing step comprises adding red blood cells to the mixture from step b, and examining the Ma-104 cells for the presence or absence of hemadsorbed red blood cells on the Ma-104 cells.

7. The method of claim 6, wherein the presence or absence of hemadsorbed red blood cells is determined within 24 hours after the red blood cells are added to the Ma-104 cell and sample mixture.

8. A composition comprising Ma-104 cells, African Swine Fever Virus (ASFV), and red blood cells.

9. The composition of claim 8, wherein the ASFV comprises the Georgia/2007 strain.

10. The composition of claim 1, wherein the Ma-104 cells are genetically unmodified.

11. The composition of claim 8, wherein the Ma-104 cells are genetically unmodified.

* * * * *